United States Patent [19]
Erlich

[11] Patent Number: 5,181,913
[45] Date of Patent: * Jan. 26, 1993

[54] CATHETER WITH CHECK VALVE AND ROLLED SHEATH

[75] Inventor: Frederick Erlich, Southfield, Mich.

[73] Assignee: PRN Services, Inc., Royal Oak, Mich.

[*] Notice: The portion of the term of this patent subsequent to Sep. 20, 2005 has been disclaimed.

[21] Appl. No.: 556,841

[22] Filed: Jul. 23, 1990

Related U.S. Application Data

[63] Continuation-in-part of Ser. No. 240,268, Sep. 6, 1988, Pat. No. 4,943,284, which is a continuation of Ser. No. 23,813, Mar. 9, 1987, Pat. No. 4,772,275.

[51] Int. Cl.⁵ .................................................. A61M 25/00
[52] U.S. Cl. .................................... 604/263; 604/247; 206/364; 206/438
[58] Field of Search ............... 604/247, 163, 171, 263, 604/280; 206/364, 438, 363, 365

[56] References Cited

U.S. PATENT DOCUMENTS

| | | | |
|---|---|---|---|
| 3,726,283 | 4/1973 | Dye et al. | 604/247 |
| 3,742,960 | 7/1973 | Dye et al. | 604/247 |
| 3,894,540 | 7/1975 | Bonner, Jr. | 604/171 |
| 3,934,721 | 1/1976 | Juster et al. | 604/171 |
| 3,967,728 | 7/1976 | Gordon et al. | 206/364 |
| 4,140,127 | 2/1979 | Cianci et al. | 604/171 |
| 4,227,533 | 10/1980 | Godfrey | 604/247 |
| 4,230,115 | 10/1980 | Walz, Jr. et al. | 604/171 |
| 4,772,275 | 10/1988 | Erlich | 604/280 |

Primary Examiner—John D. Yasko
Assistant Examiner—Anthony Gutowski
Attorney, Agent, or Firm—Weintraub, DuRoss & Brady

[57] ABSTRACT

A catheter for use in removing body fluids includes a hollow, tubular catheter with a one-way check valve disposed therein to substantially limit fluid flow therethrough to a single direction. The catheter further includes a tubular sheath disposed in a rolled-up fashion therearound to aid in sterile disposal thereof.

4 Claims, 1 Drawing Sheet

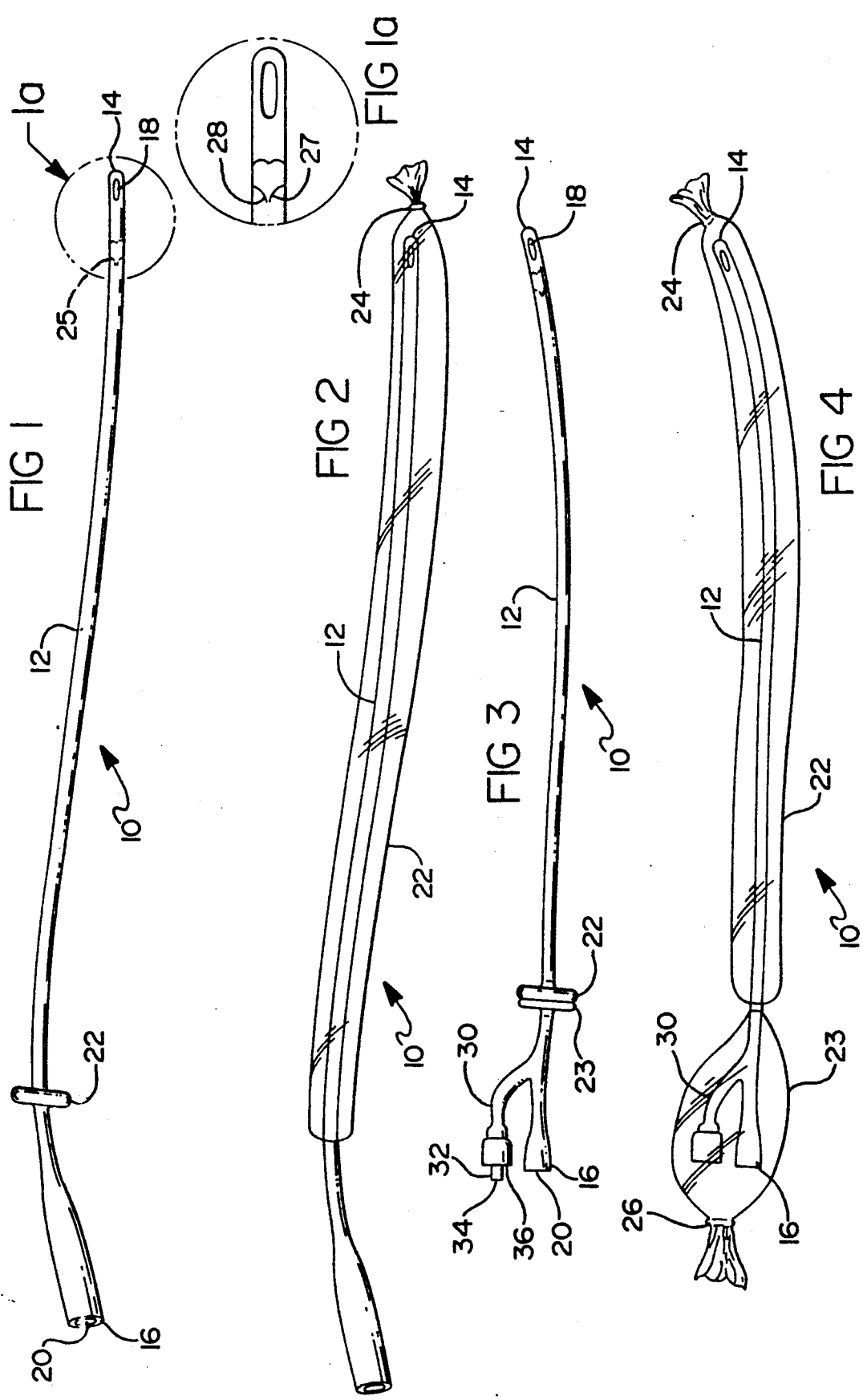

CATHETER WITH CHECK VALVE AND ROLLED SHEATH

CROSS REFERENCE TO RELATED APPLICATION

The present invention is a continuation-in-part of U.S. patent application Ser. No. 07/240,268, filed Sep. 6, 1988, which issued Jul. 24, 1990 as U.S. Pat. No. 4,943,284 which was, in turn, a continuation of Ser. No. 023,813 which issued as U.S. Pat. No. 4,772,275 filed Mar. 9, 1987.

BACKGROUND OF THE INVENTION

1. Field of the Invention

This invention relates to the field of sterile disposal of devices such as catheters, and the like used for injecting or withdrawing fluids into or from the body and, in particular, to a sheath disposed around such a device which may be drawn up to enclose the used device and tied off for sterile disposal thereof. The catheter may also have a one-way check valve incorporated therein.

2. Description of the Prior Art

Catheters and other devices for use in draining of accumulated fluids from body cavities or injecting fluids into the body have been widely used in many medical fields for a long period of time. With reference to catheters, there are numerous types and designs, any of which are particularly adapted to be inserted into a particular body cavity. For example, a urethral catheter is designed to drain urine from the bladder. A ventricular catheter is adapted to drain excess cerebrospinal fluid from the brain. A peritoneal catheter is used to drain fluid from the periotoneum; as in kidney dialysis. An enema catheter is used to introduce fluid into the gastrointestinal tract.

All of the above-mentioned types of catheters, as well as others too numerous to enumerate, have certain design features in common. A typical medicinal catheter is formed of hollow, flexible tubing. The tubing is typically comprised of a silicone elastometer such as silicone rubber, a substance which is soft and non-irritating to body tissues. A typical catheter will have a body contact and a non-body contact end. One or more inlets will be formed adjacent the body contact end. An outlet will be formed adjacent the non-body contact end, and frequently will be comprised of the non-body contact end itself. Catheters designed for different purposes may additionally comprise other structures, but the ones enumerated are generally common to all catheters. Also, the dimensions of the catheter may vary greatly and will be adapted to the purpose for which it is intended. For example, a catheter adapted as a urinary catheter may typically have an outside diameter in the range of 0.3-0.8 millimeters. In contrast, a ventricular catheter will have a much smaller diameter.

No matter the particular type, most catheters are used in a similar manner. One end of the catheter is inserted into the body cavity containing the fluid which needs to be drained. The catheter may be inserted directly through a body orifice, such as is the usual case with urethral catheters, or a special opening may have to be made. For example, an opening may have to be made into a vein and the catheter threaded through the vein until it reaches the appropriate body cavity, such as is the case with ventricular catheters. After the catheter is inserted, some means of collecting the fluid must be attached to the non-body contact end. Sometimes, as for ventricular catheters, the catheter will remain within the body and the excess fluid drained will be absorbed by another area of the body. More commonly, however, the excess fluid will simply be collected in a bag or bottle and discarded. The catheter may be left in place for long periods of time, or the excess body fluid may be drained quickly and the catheter removed after only a short period of insertion.

Irrespective of what type of catheter is used, how long it remains in place, or what type of body fluid it is used to drain, all catheters must eventually be disposed of. When the catheter is no longer needed, it will be removed from the body and then be disposed. If the catheter has been used with a patient suffering form a communicable or infectious disease, the catheter so used will be highly likely to be contaminated with an infectious agent. If such contaminated catheters are simply discarded in a casual manner, the possibility of contaminating attendant personnel and perhaps other patients is high.

The same disposal problem arises with other medical devices that come in contact with body fluids. For example, syringes are commonly used to inject or withdraw fluids from, for example, the circulatory system, the lymphatic system, the cerebrospinal system, etc. Most commonly, the syringes are disposable and used only once. Since they must be disposed of after use, the possibility of contamination from a used syringe is quite significant.

The problem of disposal of contaminated catheters and other devices is particularly acute in the management of patients afflicted with such highly infectious diseases such as Acquired Immune Deficiency Syndrome (AIDS). For diseases such as AIDS, where the exact mechanism of transmission is poorly understood, it is extremely important that attending personnel be isolated as much as possible from all potential sources of infection. Even more significantly, the apprehension by persons attending AIDS patients that they may be contaminated with the disease by the mere handling of objects used in the treatment of the patients, such as used catheters or syringes, may interfere with the ability of the attending personnel to provide proper care and treatment of the patient.

Heretofore, the only solution to the problem of sanitary disposal of catheters and other devices used in the treatment of highly infectious patients have been ad hoc, unsatisfactory ones. For example, a used catheter may be removed from the patient and immediately placed within a sterile container, such as a plastic bag, the container then being sealed. However, due to the shape of the catheter and the flexible, resilient material from which it is typically made, it is difficult to place the unwieldy catheter within the container without having to attempt to fold it or roll it up. Obviously, the motions involved in doing this cause much unnecessary and dangerous handling of the contaminated catheter.

It would be desirable to provide a means for sterile containment and subsequent disposal of a device such as a catheter which has been in contact with body fluids which minimizes handling of the contaminated object.

It would also be desirable to provide a means of disposal which could easily enclose and contain the used device by a simple, one-step unrolling motion.

It would also be highly desirable to provide a device mounted disposal means which is easy to use and has the additional advantages of being economical to manufacture and sterilize.

SUMMARY OF THE INVENTION

The device and method disclosed and claimed herein provides for easy and effective containment of a medical device such as a catheter, syringe, cannula, drainage tube, etc., the device hereof has been in contact with body fluids which is simple and inexpensive to manufacture, and may be easily disposed of. The invention provides a device for sterile disposal of devices used for injecting fluid into the body or withdrawing fluid from a body cavity, the device comprising a sheath formed of a thin, flexible, fluid impervious material which is disposed around the device in a rolled-up fashion. The sheath may be either permanently attached to the device by adhesive or sonic welding or may be snap fit thereon. The length of the sheath is such that, when it is unrolled, it will enclose the contaminated portion of the device and may be sealed off for sterile containment of the contents. With reference to an embodiment particularly suited for disposal of a catheter, the device comprises in combination a hollow, tubular catheter having at lease one inlet disposed proximate a non-body contact end; and a tubular catheter sheath disposed around the catheter medial of a body contact end thereof. The catheter may have a one way check valve therein to substantially limit fluid flow therethrough to a single direction. The check valve helps prevent spillage out of the catheter when it is removed from a patient and contains fluid therein. The length of the catheter sheath is great enough to permit it to extend beyond the body contact end of the catheter for a sufficient distance such that the body contact end may be enclosed by the sheath, with a sufficient additional length to permit ready sealing off of the contents of the sheath. The catheter sheath is disposed around the catheter in a rolled-up fashion.

To use the sheath of the instant invention, the contaminated device is first removed from the patient. The rolled-up sheath is simply unrolled to its full length. After it is unrolled, it will extend beyond the contaminated end of the used device. The end of the sheath may be then sealed to completely contain the inlet and the contaminated portion of the device therein. The device encased in the sheath may be then simply discarded. Alternatively, the sheath may be unrolled as the device is being withdrawn.

In some cases, it will be desirable to also enclose the non-body contact of the the device. This is particularly true of catheters. In most cases, the outside of the non-body contact end of the catheter will not normally be contaminated. Additionally, it is also possible that the outside of the non-body contact end of any type of catheter may become contaminated through malfunction, improper use, splashing, etc. Therefore, to provide sterile disposal of virtually the entire length of the catheter, one embodiment of the instant invention provides a second sheath disposed adjacent the first sheath and medial of the non-body contact end of the catheter. The second sheath has a length sufficiently long to enclose completely the non-body contact end of the catheter and permit subsequent sealing off of the contents of the non-body contact end of the apparatus. In order to use this embodiment, the second sheath is unrolled to enclose the non-body contact end and sealed as described above. Subsequently, the first sheath is unrolled to contain and enclose the body contact end of the catheter. Its end is then sealed off in the same manner. In a similar manner, the dual sheaths could be used to completely enclose any device contaminated along most of its length with body fluids.

In order to isolate the infectious material contained within the sheaths, it is highly desirable that they be formed of a material which is both flexible and impervious. The material should be impervious to body fluid, vapors formed thereof, atmospheric air, gases, and micro-organisms. The material must also be flexible enough to permit ready rolling up of the sheath during manufacture. Additionally, the material must be one that can be either fabricated in a sterile manner or one which can withstand sterilization after manufacture. Typical examples of such a material include: polyethylene; high density polyethylene; polypropylene; polytetrafluoroethylyne terephathalate; silicone elastomers; other synthetic organic polymers; and the like. For a device such as a syringe or where there may be a possibility of puncture of the sheath by the device, the material should also be resistant to tearing and puncture.

BRIEF DESCRIPTION OF THE DRAWINGS

The various features, advantages and other uses of this invention will become more apparent by referring to the following detailed description and drawing in which;

FIG. 1 is a perspective view partially cut away, of a device fabricated in accordance with the teachings of the instant invention showing a catheter sheath in a rolled-up position disposed around a typical catheter;

FIG. 1A is an expanded cut away view of a portion of the catheter of FIG. 1;

FIG. 2 illustrates the device of FIG. 1 with the catheter sheath having been unrolled and sealed off;

FIG. 3 is a perspective, partially cut away, view of an alternative embodiment of the device of the present invention is which a secondary sheath is provided; and FIG. 4 illustrates the device of FIG. 3 with both sheaths unrolled and sealed off.

DESCRIPTION OF THE PREFERRED EMBODIMENT

Through the following description and drawing, identical reference numerals are used to refer to the same components shown in multiple figures of the drawing.

Referring now to the drawing, and to FIG. 1 in particular, there is shown a device 10 for sterile disposal of an apparatus 12 for use in a body cavity. While the embodiments shown in the drawing are particularly adapted to catheters and syringes, it is to be understood that this is for illustrative purposes and that the instant invention is applicable to any device that comes in contact with body fluids. The apparatus 12 is hollow and tubular, and has a body contact end 14 and a non-body contact end 16. At least one inlet 18 is formed in the wall of the tubular apparatus 12 adjacent the body contact end 14 thereof. An outlet 20 is formed adjacent the non-body contact end 16 of the apparatus 12, and, as shown in FIG. 1, the outlet 20 may be formed by the non-body contact end 16. The apparatus 12 may include a one-way valve 25 to substantially limit fluid flow therethrough to a single direction. The valve 25 may consist of two or more flaps 27, 28 which allow fluid to pass from the inlet towards the outlet but which are forced closed by fluid pressure from the outlet side towards the inlet side thereof.

Disposed around and attached to the apparatus 12 is a first sheath 22. The first sheath is disposed around the apparatus 12 medial the body contact/non-body contact ends thereof. A typical placement of first sheath 22 is depicted in FIG. 1, where first sheath 22 is shown disposed around the apparatus 12 in near proximity to outlet 20. By disposing the first sheath 22 around the apparatus 12 as shown, the first sheath 22, when unrolled, will enclose and contain most of the length of apparatus 12. The first sheath 22 is attached to the apparatus 12 by a suitable means such as sonic welding, a suitable adhesive or bonding agent, etc. Alternatively, the first sheath 22 may be attached to the apparatus 12 by a snap fit.

As depicted in FIG. 1, first sheath 22 is shown rolled up around apparatus 12. FIG. 2 depicts first sheath 22 after it has been unrolled for its entire length. It will be seen from an examination of FIG. 2 that the length of first sheath 22 is long enough such that it will extend beyond the body contact end 14 of apparatus 12. The extension of first sheath 22 beyond the body contact end 14 will permit the sealing off thereof to enclose the contents of first sheath 22. Means of sealing 24 is provided to seal off the end of first sheath 22 to completely enclose the contents thereof. Means of sealing 24 may be in conventional type of sealing means, such as a paper coated wire twist tie, a rubber band, adhesive tape, a slip-on closure, a spring clip, etc. Alternatively, the end of sheath 22 may be provided with a self-sealing means such as a lip and groove formed therein.

The method of use of the device 10 for sterile disposal of a used device, e.g., a catheter will now be described. First, it is desirable that device 10 be made sterile prior to use. The device 10 may be either manufactured in a manner such that it is sterile or that it may be sterilized after manufacture by any conventional method. Prior to use, the first sheath 22 will be in the rolled up position shown in FIG. 1.

The catheter is used in the conventional manner by inserting the body contact end 14 with the inlet 18 formed therein into a body cavity (not shown). The outlet 20 of the apparatus 12 will be attacted to a means (not shown) for storing the unwanted fluids. In certain cases, outlet 20 may be first connected with an auxiliary tube (not shown) which is in turn connected to the storage means.

After the body fluid has been drained, the catheter will be removed from the body cavity by removing body contact end 14 carrying inlet 18 therefrom. The outlet 20 disposed on non-body contact end 16 will be then detached from the storage means and/or auxiliary tube. The first sheath 22 will then be unrolled by grasping it and pulling it towards body contact end 14. After it is fully unrolled and extends beyond the body contact end 14 of the apparatus 12, it will be sealed off by applying sealing means 24. FIG. 2 illustrates the range of the device of the instant invention after the steps of unrolling and sealing off have been performed. It may be seen from an examination of FIG. 2 that the contaminated portions of the apparatus 12, including particularly inlet 18, are fully contained within the sealed off first sheath 22. Since the catheter was in use, the surface exposed during the unrolling procedure will not have been exposed to the contaminated body fluids. Thus, the impervious area provided by the unrolled and sealed off first sheath 22 will effectively prevent cross-contamination between used catheter any any other object, such as other hospital equipment or another patient or attendant.

Alternately, the first sheath 22 may be unrolled as the apparatus 12 is being withdrawn from the body. It is then sealed off as described above. This alternate method provides even stronger protection against the possibility of contamination.

Another embodiment of the device of the instant invention is illustrated in FIGS. 3 and 4. The apparatus 12 shown in FIG. 3 has the additional structure of a branch 30 formed near the non-body contact end 16 of the apparatus 12. The branch 30 is hollow and tubular and is in fluid communication with apparatus 12. A hollow, rigid member 32 is shown partially inserted into the end of branch 30. Disposed within hollow, rigid insert 32 ia a plug 34 comprised of softer material, tyically silicone rubber. A rubber band 36 is shown disposed on the outside of branch 30 to hold rigid insert 32 and plug 34 in correct position. The purpose of the additional structures shown is so that the needle of a syringe (not shown) may be inserted into apparatus 12 by plunging it into plug 34. By means of the syringe, several additional functions may be added to the functioning of the catheter. For example, if additional suction is needed to withdraw the body fluids from the cavity, the suction may be supplied by means of a syringe. Conversely, medication may be inserted into the body cavity by means of the syringe.

In FIGS. 3 and 4, a second sheath 23 is provided. FIG. 3 illustrates the second sheath 23 in its rolled-up position. Second sheath 23 is disposed immediately adjacent first sheath 22 and medially of the non-body contact end 16 of apparatus 12. As with first sheath 22, the length of second sheath 23 is such that, when second sheath 23 is fully unrolled, a portion thereof will extend beyond the non-body contact end 16 of apparatus 12. Second sheath 23, upon being unrolled, may then be sealed off with sealing means 26 in a manner analogous to sheath 22.

FIG. 4 depicts the device of FIG. 3 with both sheaths 22, 23 unrolled and sealed off. It may be seen from an examination of FIG. 4 that virtually the entire length of apparatus 12 is encased by sheaths 22, 23 thereby preventing contamination from virtually any part of apparatus 12 from reaching the environment outside the sheaths 22, 23. Sterile containment of the entire apparatus 12 may be necessary in cases where both ends 14, 16 thereof are likely to become contaminated.

Having, thus, described the invention, what is claimed is:

1. A disposable device for a single time transfer of body fluids comprising:
   a hollow, tubular catheter having a first end and a second end, and having at least one inlet disposed proximate the first end thereof and at least one outlet disposed proximate the second end;
   a check valve disposed in the catheter for substantially limiting the fluid flow therethrough to a single direction;
   a tubular normally rolled-up sheath disposed around the catheter medial the first end and the second end, the sheath being unrollable with a portion thereof extending past the first end of the catheter after use;
   means for sealing the portion of sheath extending beyond the first end of the catheter after the sheath is unrolled; and wherein substantially the entire portion of the tubular catheter is enclosable and sealable within the sheath after use.

2. The device of claim 1, wherein the sheath is formed of a flexible, puncture-resistant material.

3. The device of claim 2, wherein the puncture-resistant material is substantially impervious to body fluids, vapors thereof, air, gases, and microorganisms.

4. The device of claim 1, wherein all of the components of the device are in a sterile condition prior to use.

* * * * *